United States Patent [19]
Weltman et al.

[11] Patent Number: 6,048,726
[45] Date of Patent: Apr. 11, 2000

[54] INHIBITION OF EXPRESSION OF INTERLEUKIN-5

[76] Inventors: Joel K. Weltman, 4 Wildacre La., Barrington, R.I. 02806; Aftab S. Karim, 45 Sunset Ave., Farmingdale, N.Y. 11735

[21] Appl. No.: 09/079,839

[22] Filed: May 15, 1998

[51] Int. Cl.$^7$ .............................. C12N 5/06; C07H 21/00
[52] U.S. Cl. ............................................ 435/375; 536/24.5
[58] Field of Search .......................... 435/375, 6; 514/44; 536/24.5, 24.3, 24.31

[56] References Cited

U.S. PATENT DOCUMENTS

| | | | |
|---|---|---|---|
| 5,514,788 | 5/1996 | Bennett et al. | 536/23.1 |
| 5,591,623 | 1/1997 | Bennett et al. | 435/240.2 |
| 5,616,488 | 4/1997 | Sullivan et al. | 435/366 |
| 5,681,936 | 10/1997 | Nicholson | 530/416 |
| 5,728,820 | 3/1998 | Akerblom | 536/23.5 |
| 5,744,166 | 4/1998 | Illum | 424/501 |

OTHER PUBLICATIONS

Antisense '97: A roundtable on the state of the industry. Nature Biotechnol. 15: 519–524, Jun. 1997.

De Mesmaeker et al. Antisense Oligonucleotides. Acc. Chem Res. 28: 366–374, Sep. 1995.

Faccioli et al. IL–5 drives eosinophils from bone marrow to blood and tissues in a guinea–pig model of visceral larva migrans syndrome. Mediators of Inflammation 5: 24–31, Jan. 1996.

Gewirtz et al. Facilitating oligonucleotide delivery: Helping antisense deliver on its promise. Proc. Natl. Acad. Sci. USA 93: 3161–3163, Apr. 1996.

Gura. Antisense has growing pains. Science 270:575–577, Oct. 1995.

Rojanasakul. Antisense oligonucleotide therapeutics: Drug delivery and targeting. Adv. Drug Delivery Reviews 18: 115–131, 1996.

Azuma et tal., "Cloning of cDna for human T–cell replacing factor (interleukin–5) and comparison with the murine homologue", *Nucleic Acids Res.* 14(22):9149–58 (1986).

Agrawal et al., "Site specific functionalization of oligonucleotides for attaching two different reporter groups", *Nucleic Acids Res.* 18:5419–5423 (1990).

Cosstick et al., "Fluorescent labelling of tRNA and oligodeoxynucleotides using T4 RNA ligase", *Nucleic Acids Res.* 12:1791–1810 (1984).

Eckstein et al., "Phosphorothioates in molecular biology," *TIBS* 14:97–100 (1989).

Edwards, "Polarizability, Basicity and Nucleophilic Character", *J. Amer. Chem. Soc.* 78:1819–21 (1956).

Fidanza et al., "Introduction of Reporter Groups at Specific Sites in DNA Containing Phosphorothioate Diesters", *J. Am. Chem. Soc.* 111:9117–9119 (1989).

Frey et al., "Bond Order and Charge Localization in Nucleoside Phosphorothioates", *Science* 228:541–45 (1985).

Geary et al., "Antisense oligonucleotide inhibitors for the treatment of cancer: 1. Pharmacokinetic properties of phosphorothioate oligodeoxynucleotides", *Anti–cancer Drug Des.* 12:383–93 (1997).

Ginobbi et al., "Folic Acid–Polylysine Carrier Improves Efficacy of c–myc Antisense Oligodeooxynucleotides on Human Melanoma (M14) Cells", *Anticancer Res.* 17:29–35 (1997).

Gish et al., "DNA and RNA Sequence Determination Based on Phosphorothiaoate Chemistry", *Science* 240:1520–22 (1988).

Goody et al., "Thiophosphate Analogs of Nucleoside Di– and Triphosphate", *J. Am. Chem. Soc.* 93:6252–57 (1971).

Henry et al., "Antisense oligonucleotide inhibitors for the treatment of cancer: 2. Toxicological properties of phosphorothioate oligodeoxynucleotides", *Anti–cancer Drug Des.* 12:395–408 (1997).

Hodges et al., "Post–Assay" Covalent Labeling of Phosphorothioate–Containing Nucleic Acids with Multiple Fluorescent Markers, *Biochem.* 28:261–67 (1989).

Karim et al., "Maleimide–mediated protein conjugates of a nucleoside triphosphate gamma–S and an internucleotide phosphorothioate diester", *Nucleic Acids Res.* 23:2037–2040 (1995).

Sharma et al., "The NF–kB Transcription Factor in Oncogenesis", *Anticancer Res.* 16:589–96 (1996).

Weltman et al., "Selection of Antisense Sequences Against Human Interleukin–5 by Maximization of G+C Content", (posted Apr. 3, 1998, visited Apr. 23, 1998) <http://www-.faseb.org/asbmb/asbmb98/f2657.html>.

"Hybridon Signs Research Collaboration with Leading Medical Institutions In Paris and Oslo to Develop Antisense Therapies for Asthma and Cancer" visited May 15, 1998 <http://www.hybridon.com/graphic_ye . . . o/news_releases/news96/090996.html>.

*Primary Examiner*—John S. Brusca
*Assistant Examiner*—Thomas G. Larson
*Attorney, Agent, or Firm*—Fish & Richardson P.C.

[57] ABSTRACT

A method of inhibiting interleukin-5 expression using an antisense oligonucleotide which contains at least one non-natural internucleoside linkage.

11 Claims, 4 Drawing Sheets

6,048,726

```
SEQUENCE LISTING

<160> NUMBER OF SEQ ID NOS: 2

<210> SEQ ID NO 1
<211> LENGTH: 16
<212> TYPE: DNA
<213> ORGANISM: Homo sapiens

<400> SEQUENCE: 1
actcaaatgc agaagc                                                          16

<210> SEQ ID NO 2
<211> LENGTH: 816
<212> TYPE: DNA
<213> ORGANISM: Homo sapiens

<400> SEQUENCE: 2
atgcactttc tttgccaaag gcaaacgcag aacgtttcag agccatgagg atgcttctgc      60
atttgagttt gctagctctt ggagctgcct acgtgtatgc catccccaca gaaattccca     120
caagtgcatt ggtgaaagag accttggcac tgctttctac tcatcgaact ctgctgatag     180
ccaatgagac tctgaggatt cctgttcctg tacataaaaa tcaccaactg tgcactgaag     240
aaatctttca gggaataggc acactggaga gtcaaactgt gcaagggggt actgtggaaa     300
gactattcaa aaacttgtcc ttaataaaga aatacattga cggccaaaaa aaaaagtgtg     360
```

| | | | | | |
|---|---|---|---|---|---|
| gagaagaaag | acggagagta | aaccaattcc | tagactacct | gcaagagttt | cttggtgtaa | 420 |
| tgaacaccga | gtggataata | gaaagttgag | actaaactgg | tttgttgcag | ccaaagattt | 480 |
| tggaggagaa | ggacatttta | ctgcagtgag | aatgagggcc | aagaaagagt | caggccttaa | 540 |
| ttttcaatat | aatttaactt | cagagggaaa | gtaaatattt | caggcatact | gacactttgc | 600 |
| cagaaagcat | aaaattctta | aaatatattt | cagatatcag | aatcattgaa | gtattttcct | 660 |
| ccaggcaaaa | ttgatatact | tttttcttat | ttaacttaac | attctgtaaa | atgtctgtta | 720 |
| acttaatagt | atttatgaaa | tggttaagaa | tttggtaaat | tagtatttat | ttaatgttat | 780 |
| gttgtgttct | aataaaacaa | aaatagacaa | ctgttc | | | 816 |

INHIBITION OF EXPRESSION OF INTERLEUKIN-5

BACKGROUND OF THE INVENTION

The invention relates to treatment of inflammatory diseases.

Asthma is an episodic disease characterized by narrowing of air passages which may be induced by such factors as exposure to allergens, exercise, and stress. Acute episodes of asthma, which represent one of the most common respiratory emergencies, can be followed by long periods of time during which a patient may be essentially symptom free. However, in some cases, a patient may experience some degree of airway obstruction and difficulty in breathing daily.

Approximately 5 per cent of adults and 7–10% of children are estimated to be affected by asthma. Conventional treatments for asthma include bronchodilating agents such as beta-adrenergic agonists and methylxanthines, e.g., theophylline. Glucocorticoids may also be administered to reduce airway inflammation.

SUMMARY OF THE INVENTION

The invention provides a method of inhibiting eosinophilic inflammation in a mammal by administering to the mammal a compound which inhibits expression of interleukin-5 (IL-5). Preferably, the compound is nucleic acid molecule such as an IL-5 antisense DNA, the sequence of which is complementary to a coding sequence of IL-5. For increased resistance to degradation and improved uptake by cells, the nucleic acid compound contains at least one non-natural internucleotide linkage. By the term "non-natural internucleotide linkage" is meant an internucleotide bond that differs from a phosphate diester (PO) bond. For example, a non-natural internucleotide linkage may be a bridging phosphorothioate (PS) internucleotide linkage or a non-bridging phosphoroamidate (PN) internucleotide linkage.

Expression of IL-5 is inhibited by contacting mammalian cells, e.g., immune cells at the site of inflammation, with IL-5 antisense DNA, e.g., a synthetic IL-5 antisense oligonucleotide. For example, IL-5 antisense nucleic acid is introduced into T lymphocytes, mast cells, or eosinophils, which naturally produce IL-5. Binding of the antisense nucleic acid to an IL-5 transcript in the target cell results in a reduction in IL-5 production by the cell. By the term "antisense nucleic acid" is meant a nucleic acid (RNA or DNA) which is complementary to a portion of an mRNA, and which therefore hybridizes to and prevents translation of the mRNA. Preferably, the antisense DNA is complementary to the 5' regulatory sequence or the 5' portion of the coding sequence of IL-5 mRNA (e.g., a sequence encoding a signal peptide). Standard techniques of introducing antisense DNA into the cell may be used, including those in which antisense DNA is a template from which an antisense RNA is transcribed. The method is preferably used in situations in which expression of IL-5 is upregulated, e.g., as a result of an allergic reaction or other immune response. For example, IL-5 production is increased in allergy-induced asthma as well as in patients undergoing parasitic infections.

IL-5 antisense DNA preferably has one or more of the following properties. At least one (preferably two or more) internucleotide linkage of the IL-5 antisense DNA is a PS diester linkage. The G+C content of the IL-5 antisense DNA is preferably at least 25%, more preferably at least 35%, and most preferably at least 40% G+C. For example, the nucleotide sequence of SEQ ID NO:1 has a G+C content of 43%. The length of the oligonucleotide is at least 10 nucleotides. Preferably, the length is between 10 and 50 nucleotides, inclusive. More preferably, the length is between 10 and 20 nucleotides, inclusive (e.g., the length of SEQ ID NO:1 is 16 nucleotides).

The sequence of the IL-5 antisense DNA is complementary to an IL-5 coding sequence within exon 1 of mammalian IL-5 genomic DNA, e.g, a sequence that is complementary to IL-5 coding sequence encoding a signal peptide. Most preferably, the sequence of the IL-5 antisense DNA is 5' ACTCAAATGCAGAAGC 3' (SEQ ID NO:1).

IL-5 antisense therapy is preferably administered to a mammal that is characterized as suffering from asthma or allergic rhinitis. These conditions are treated by administering an IL-5 inhibitory compound, e.g., an IL-5 antisense DNA, inhaled orally or intranasally (respectively). IL-5 antisense therapy is also useful to treat a mammal characterized as suffering from allergic conjunctivitis or atopic eczema. Topical administration of a compound that reduces IL-5 production is preferable for treatment of conjunctivitis or inflammatory skin diseases such as eczema.

The invention also features an oligonucleotide, e.g., an antisense oligonucleotide, containing at least one non-bridging phosphoroamidate internucleotide linkage.

Other features and advantages of the invention will be apparent from the following description of the preferred embodiments thereof, and from the claims.

DESCRIPTION OF THE PREFERRED EMBODIMENTS

Figure 1:
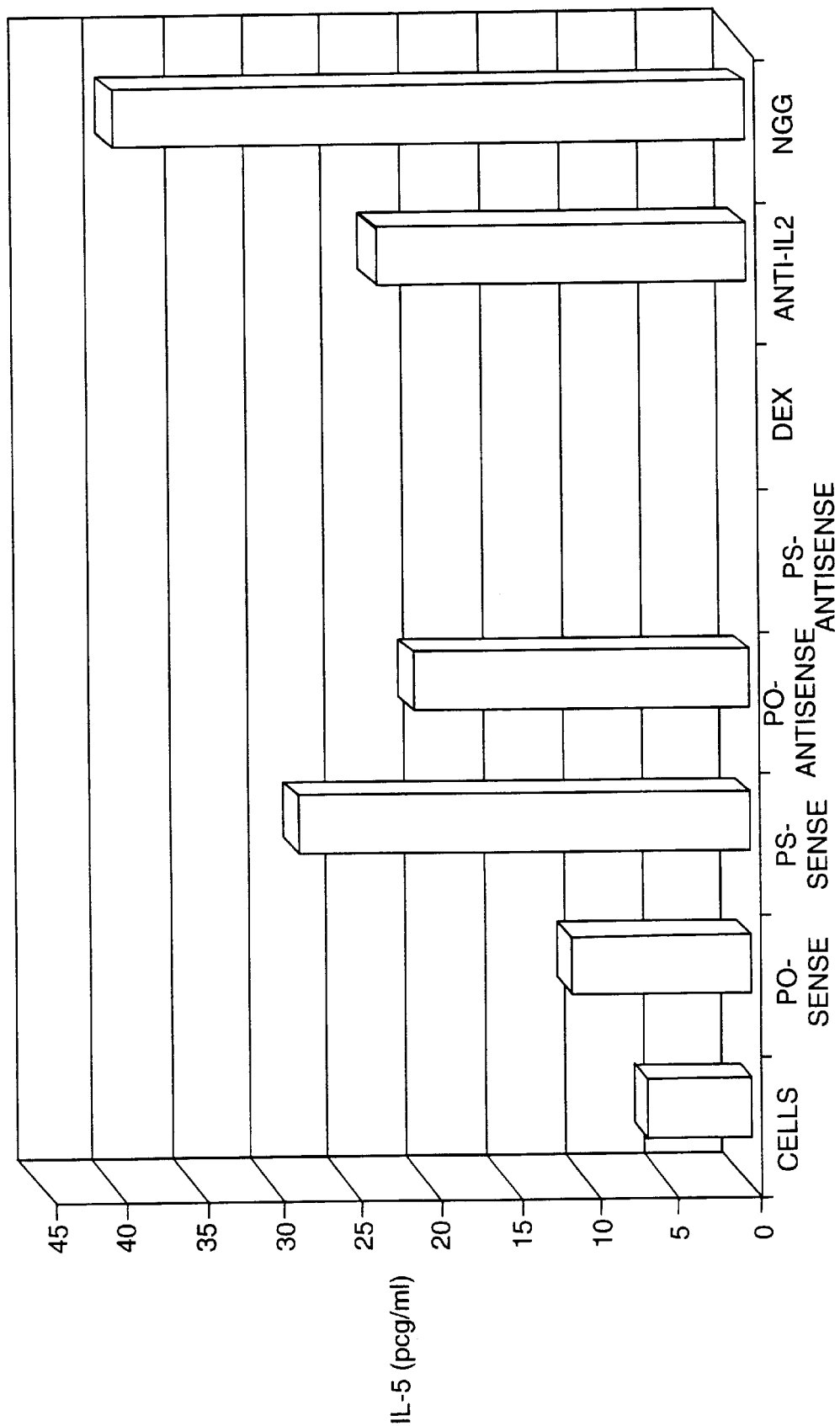
FIG. 1 is a bar graph showing inhibition of IL-5 expression using IL-5 antisense oligonucleotides.

Antisense nucleic acids which inhibit the expression of IL-5 are used to treat pathological conditions characterized by IL-5-mediated eosinophilic inflammation such as that associated with asthma and eczema. Preferred oligonucleotides have a high G+C content (e.g., at least 25% G+C).

Human IL-5 genomic DNA (GenBank Accession number JO2971) has 4 exons. The sequence of the IL-5 antisense DNA is preferably complementary to an IL-5 coding sequence within exon 1 of mammalian IL-5 genomic DNA (i.e., the sequence is in the 5'portion of the coding sequence, e.g., in DNA encoding the signal sequence portion of IL-5). The nucleotide sequence of human IL-5 cDNA (GenBank Accession number XO4688) is shown in Table I.

TABLE I

```
  1 atgcactttc tttgccaaag gcaaacgcag aacgtttcag agccatgagg atgcttctgc
 61 atttgagttt gctagctctt ggagctgcct acgtgtatgc catcccaca gaaattccca
121 caagtgcatt ggtgaaagag accttggcac tgctttctac tcatcgaact ctgctgatag
181 ccaatgagac tctgaggatt cctgttcctg tacataaaaa tcaccaactg tgcactgaag
241 aaatctttca gggaataggc acactggaga gtcaaactgt gcaaggggt actgtggaaa
301 gactattcaa aaacttgtcc ttaataaaga aatacattga cggccaaaaa aaaagtgtg
361 gagaagaaag acggagagta aaccaattcc tagactacct gcaaagttt cttggtgtaa
421 tgaacaccga gtggataata gaaagttgag actaaactgg tttgttgcag ccaaagattt
481 tggaggagaa ggacatttta ctgcagtgag aatgagggcc aagaaagagt caggccttaa
541 ttttcaatat aatttaactt cagagggaaa gtaatattt caggcatact gacactttgc
601 cagaaagcat aaaattctta aaatatattt cagatatcag aatcattgaa gtattttcct
661 ccaggcaaaa ttgatatact tttttcttat ttaacttaac attctgtaaa atgctgtta
721 acttaatagt atttatgaaa tggttaagaa tttggtaaat tagtatttat ttaatgttat
781 gttgtgttct aataaaacaa aaatagacaa ctgttc (SEQ ID NO:2)
```

The oligonucleotide has been chemically derivitized, e.g., by introducing one or more phosphorothioate diester linkages or phosphoramidate linkages, to (1) reduce susceptibility to nuclease degradation, (2) reduce the negative charge, or (3) increase lipophilicity (thereby increasing cell uptake).

EXAMPLE 1
Antisense Oligonucleotides Specific for Human IL-5 Inhibits IL-5 Production by Human Primary Inflammatory Cells IL-5 is a major mediator of eosinophilic inflammation in asthma and other allergic diseases. IL-5 expression, e.g., in patients suffering from asthma, is reduced by administering to the patient IL-5 antisense nucleotide by inhalation therapy. IL-5 synthesis by cellular infiltrates in the lungs is decreased by sequence-specific inhibition of IL-5 mRNA. An IL-5 antisense sequence (5'-ACTCAAATGCAGAAGC-3'; SEQ ID NO:1) was synthesized with standard phosphodiester linkages (PO) and with phosphorothioate (PS) linkages at positions 3 and 8 (5'-ACT*CAAAT*GCAGAAGC-3', where the "*" represents a bridging PS linkage). IL-5 expression by human primary peripheral blood mononuclear cells was determined in vitro as described below:

Three 150 mg/5 ml (3% weight:volume) solutions of bovine gelatin (DIFCO Product #0143-15-1 and Lot #112536JJ) were prepared in RPMI-1640 Medium (Sigma Product #R-8758 and Lot #97H2374). The suspensions were heated on stirrer-heater plate.

Three vials of 10 ml of human blood were collected in heparinized tubes. Each 10 ml blood volume was added to 5 ml of gelatin suspension and allowed to rest at room temperature for 45 minutes. The buffy coats were removed and combined. The cells of the combined buffy coats were centrifuged, and the supernatant was discarded. The cell pellet was suspended in 10 ml of Super Tissue Medium prepared with RPMI1640 Medium (Sigma Product #R-8758) and fetal bovine serum (Sigma Product #F-2442 and Lot #97H8412) and Triple ABX therapy (Pen-Strep-Neo, Sigma Product #P-3664 and Lot #57H4633). 10 ml of Fetal bovine serum and 1 ml of a standard Pen-Strep-Neo solution was added to 90 ml of RPMI 1640 according to standard protocols.

200 microliters of the 10 ml stock cell suspension were added to forty-five 500 microliter sterile skirted tubes with screw caps (Sigma Product #Z37-216-1 and Lot #97H1207). Sense and antisense IL-5 oligonucleotides were made by and purchased from Tri-Link (San Diego, Calif.). IL-5 sense oligonucleotides were made in the PO form and the derivitized (PS) form (in the PS IL-5 sense oligonucleotides, the A's were PS). IL-5 antisense oligonucleotides were also made in the PO and PS form (T's were PS).

Oligonucleotide stock solutions were prepared in distilled water at a concentration of 300 OD units/ml ($2\times10^{-3}$M). Stock was diluted in Super Medium to yield a final concentration of $2\times10^{-4}$M concentration of all four oligonucleotides for IL-5 expression assays. For dose-response assays, the PO and PS IL-5 antisense oligonucleotides were further diluted in Super Medium at the following concentrations: $1\times10^{-4}$M, $1\times10^{-5}$M, and $1\times10^{-7}$M.

1 mg of an anti-inflammatory agent, dexamethasone (Sigma Product #D-8893, Lot #116H4656), was dissolved in 25 ml of Super medium to yield a $1\times10^{-4}$M solution. A further 1:10 dilution of this stock was performed in Super Medium to yield a solution with a concentration of $1\times10^{-5}$ M dexamethasone.

An antibody specific for human IL-2 was purchased from R&D system (R&D Product #AB-202-NA and Lot #AN046121) 1 mg anti-IL-2 antibody and 1 mg Normal Goat Globulin (R&D Product #AB-108-C and Lot #ES207031) were diluted in Super Medium to yield a solution with a protein concentration of 1 mg/ml.

A representative experiment was carried out as follows. Stock Sense oligonucleotides, stock antisense oligonucleotides, stock dexamethasone, and stock immunoglobulin preparations were added to a test tube containing the cell suspension. As a control, cells were incubated in tissue culture medium alone. Each combination was done in triplicate.

1: 200 ml of cell suspension+20 ml medium.
2: 200 ml of cell suspension+20 ml medium.
3: 200 ml of cell suspension+20 ml stock ($2\times10^{-4}$M) PO sense.
4: 200 ml of cell suspension+20 ml stock ($2\times10^{-4}$M) PS sense.
5: 200 ml of cell suspension+20 ml stock ($2\times10^{-4}$M) PO antisense.
6: 200 ml of cell suspension+20 ml stock ($2\times10^{-4}$M) PS antisense.
7: 200 ml of cell suspension+20 ml stock ($1\times10^{-4}$M) PO antisense.
8: 200 ml of cell suspension+20 ml stock ($1\times10^{-4}$M) PS antisense.
9: 200 ml of cell suspension+20 ml stock ($1\times10^{-5}$M) PO antisense.
10: 200 ml of cell suspension+20 ml stock ($1\times10^{-5}$M) PS antisense.
11: 200 ml of cell suspension+20 ml stock ($1\times10^{-6}$M) PO antisense.
12: 200 ml of cell suspension+20 ml stock ($1\times10^{-6}$M) PS antisense.
13: 200 ml of cell suspension+20 ml $1\times10^{-5}$M Dexamethasone.

14: 200 ml of cell suspension+20 ml of 1 mg/ml anti-IL-2 antibody.
15: 200 ml of cell suspension+20 ml of 1 mg/ml NGG.
16: Super tissue culture medium with no cells.

In samples 3–6, the final concentration of oligonucleotide was 20 mM; in samples 7–8, the final concentration of oligonucleotide was 10 mM; in samples 9–10, the final concentration of oligonucleotide was 1 mM; in samples 11–12, the final concentration of oligonucleotide was 0.1 mM; in sample 13, the final concentration of Dexamethasone was 1 mM; in samples 14–15, the final concentration of immunoglobulin was 100 micrograms/ml. Samples 1–16 were placed in an incubator (37° C.) for 16 hours in the dark. Samples 2–15 were then stimulated with 50 ml of Phorbol/PHA solution prepared as described below. Tube 1 was left unstimulated by addition of 50 ml of tissue culture medium. Tube 16 was kept as a control that contained neither cells nor stimulant (medium alone).

The PMA/PHA stock solution was prepared as follows: 1 mg PMA (Sigma Product #P-8139, Lot #107H0384) was added to 1 ml of distilled $H_2O$ to yield a concentration of 2.3 mg/ml. This solution was diluted 20-fold in super medium to yield a concentration 100 ng/ml. 5 mg of PHA (Sigma Product #L-9132, and Lot #47H4665) was dissolved in 1 ml of super medium to yield a concentration of 5 mg/ml. This solution was diluted 100-fold in super medium to yield a concentration of 50 mg/ml. 2 mls of PMA (100 ng/ml) were added to 2 mls of PHA (50 mg/ml) to yield a stock PMA concentration of 50 ng/ml and a PHA concentration of 25 mg/ml. 50 ml of this PMA/PHA solution was added to each of samples 2–15. The final concentration of PMA in tubes 2–15 was 10 ng/ml, and the final concentration of PHA in tubes 2–15 was 5 mg/ml.

Tubes 1–16 in triplicate were again placed in the incubator for 24 hours in the dark at 37° C. All of the samples were then centrifuged, and the supernatants were placed in 48 fresh tubes. The tubes were frozen overnight and analyzed for IL-5 production using a standard ELISA assay.

Figure 2:
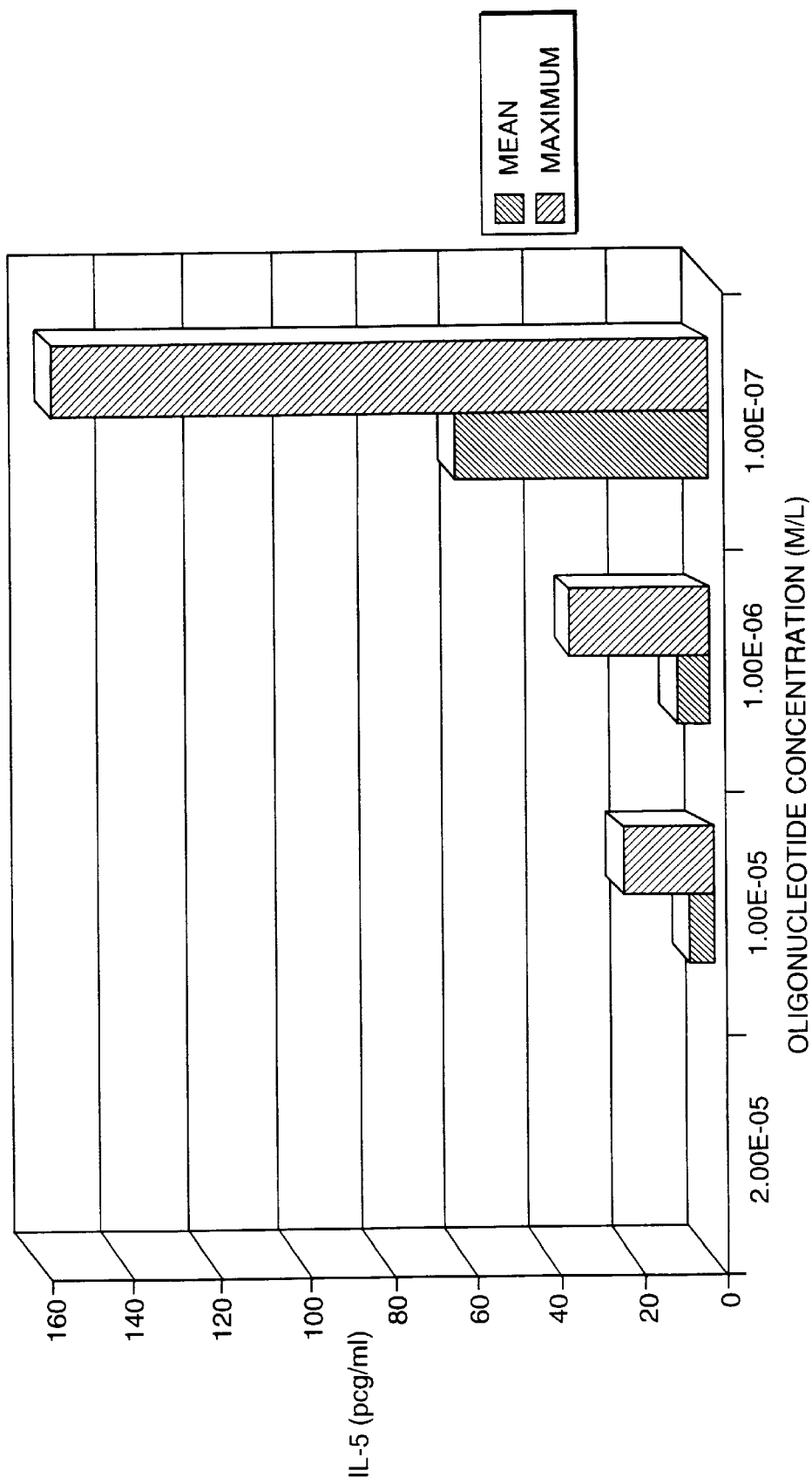
FIG. 2 is a bar graph showing inhibition of IL-5 expression using IL-5 antisense oligonucleotides relative to concentration of oligonucleotide administered to target cells.

As shown in FIG. 1, the 16-mer PS-antisense at 20 micromolar concentration resulted in complete inhibition of IL-5 secretion. Furthermore, inhibition of IL-5 secretion was found to be dose-dependent (FIG. 2). The inhibitory effect of PS-antisense on IL-5 secretion was statistically significant, both by ANOVA analysis as well as paired t-tests.

The presence of a PS linkage in an oligonucleotide may lead to chirality which has been associated with decreased efficiency of hybridization or antisense activity. However, this problem was not observed with the oligonucleotides tested. Presence of a PN linkage in an oligonucleotide reduces chirality. The IL-5 antisense oligonucleotides tested were found to have potent and dose-dependent antisense activity in treated cells.

These data indicate that a PS-antisense oligonucleotide which has a nucleotide sequence that is complementary to IL-5 -encoding DNA inhibits IL-5 expression in human cells which mediate inflammation. Thus, such antisense molecules are useful as anti-asthma and anti-allergy therapeutics and to treat other pathological conditions that involve eosinophilic inflammation, e.g., eczema.

EXAMPLE 2
Methods of Therapy

Patients with pathologic eosinophilic inflammation such those suffering from asthma or eczema can be treated by administering IL-5 antisense nucleic acids.

Antisense therapy is used to inhibit expression of IL-5, the main regulator of eosinophils, in pathologic conditions characterized by eosinophilia. For example, an IL-5 antisense strand (either RNA or DNA) is directly introduced into the cells in a form that is capable of binding to the mRNA transcripts. Alternatively, a vector containing sequence which, which once within the target cells, is transcribed into the appropriate antisense mRNA, may be administered. Antisense nucleic acids which hybridize to mRNA decrease or inhibit production of the polypeptide product encoded by a gene by associating with the normally single-stranded mRNA transcript, thereby interfering with translation and thus, expression of the protein.

Antisense therapy may be carried out by administering to a patient an antisense nucleic acid by standard vectors and/or gene delivery systems. Suitable gene delivery systems may include liposomes, receptor-mediated delivery systems, naked DNA, and viral vectors such as herpes viruses, retroviruses, adenoviruses and adeno-associated viruses, among others.

As is discussed above, undesired or pathological inflammation such as that associated with asthma or eczema can be treated by inhibiting IL-5 expression. A reduction in IL-5 productions results in a decrease in inflammation and improvement of the clinical symptoms of these diseases. A therapeutic composition may include one or more compounds, e.g., nucleic acids or immunosuppressive agents, and a pharmaceutically acceptable carrier. The therapeutic composition may also include a gene delivery system as described above. Pharmaceutically acceptable carriers are biologically compatible vehicles which are suitable for administration to an animal: e.g., physiological saline. A therapeutically effective amount of a compound is an amount which is capable of producing a medically desirable result such as reduced inflammation or inhibition of eosinophilia in a treated animal, e.g., by inhibition of expression of a target gene such as IL-5.

Parenteral administration, such as intravenous, subcutaneous, intramuscular, and intraperitoneal delivery routes, may be used to deliver the nucleic acids. For treatment of asthma, inhalation therapy is preferred. For treatment of eczema, topical application is preferred. Dosages for any one patient depends upon many factors, including the patient's size, body surface area, age, the particular nucleic acid to be administered, sex, time and route of administration, general health, and other drugs being administered concurrently. Dosage for intravenous administration of nucleic acids is from approximately $10^6$ to $10^{22}$ copies of the nucleic acid molecule.

EXAMPLE 3
Semi-Empirical Hückel Molecular Orbital Analysis of Internucleotide Phosphorothioate Diesters Oligonucleotides that contain internucleotide phosphorothioate diesters rather than standard phosphate diesters are useful as therapeutic agents because they are more nuclease resistant than their standard counterparts. Calculations reported herein, performed by the Hückel molecular orbital method, show that the energy of the highest occupied molecular orbital (HOMO) of an internucleotide phosphorothioate diester is 15.9 kcal/mole higher than that of the corresponding HOMO of the standard internucleotide phosphate diester with the same sequence. The electron density in the phosphorothioate HOMO is almost completely centered on the sulfur atom. The results of this parametricized Hückel molecular orbital analysis are consistent with the model of the internucleotide phosphorothioate sulfur as a soft nucleophile. The methods described herein are useful to predict reactivity of phosphothioates with electrophiles.

A semi-empirical Hückel molecular orbital analysis of internucleotide phosphorothioate diesters was carried out as follows. Molecular orbital calculations were performed by a standard semi-empirical method modified for heteroatoms (e.g., the methods described in Roberts, J. D., 1962, Notes on Molecular Orbital Calculations, New York, W A Benjamin, pp.77–81; Streitwieser, A., 1961, Molecular Orbital Theory for Organic Chemists, New York, Wiley, pp63–134; and Pullman et al., 1963, Quantum Biochemistry, New York, Interscience Publishers, pp. 148–150). HMO models of internucleotide phosphate diesters and phosphorothioate diesters were expressed as secular determinants. Eigenvalues and eigenvectors were calculated for matrix representations of the secular determinants using MATLAB (The Mathworks, Natick, Mass.).

Figure 3:
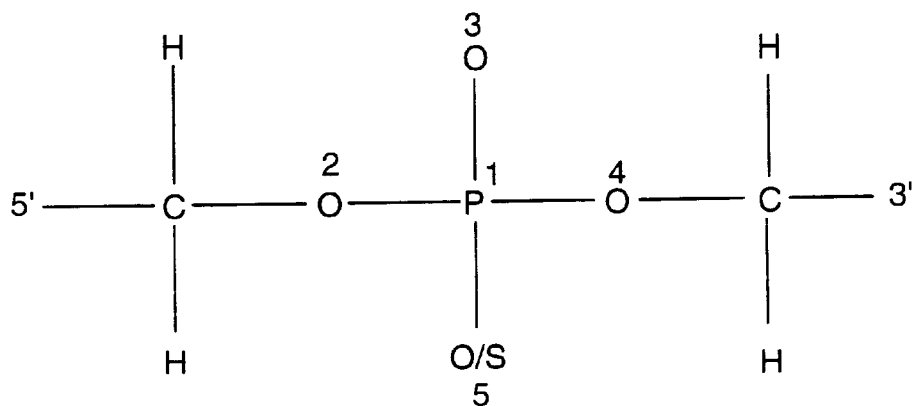
FIG. 3 is a diagram showing the numbering of internucleotide phosphate and phosphorothioate diesters.

The numbering system shown in FIG. 3 was used for the atoms of internucleotide phosphate and phosphorothioate diesters. Atom number 5 is an oxygen in the phosphate diester; in the phosphorothioate diester, atom number 5 is a sulfur.

The secular determinant for the nucleotide diester is shown in Table II.

TABLE II

| X + h1 | k2 | k3 | k4 | k5 |
|---|---|---|---|---|
| k2 | x + h2 | 0 | 0 | 0 |
| k3 | 0 | x + h3 | 0 | 0 |
| k4 | 0 | 0 | x + h4 | 0 |
| k5 | 0 | 0 | 0 | x + h5 |

The values used for the Coulomb integral parameters (h) were as follows: h1=–0.2, h2=h4=1.6 and h3=0.8. The values used for the bond integral parameters (k) were: k2=k4=0.8 and k3=0.7. For the phosphate diester, the following values were used for the parameters of atom 5: h5=0.8 and k5=0.7. For the phosphorothioate diester, the following values were used for the parameters of atom 5: h5=0 and k5=0.1.

The energy levels of the π-electron orbitals calculated for the internucleotide phosphorothioate diester and the internucleotide phosphate diester are given in Table III. Orbital energy is expressed in units of β, where β equals –20 kcal/mol.

TABLE III

| Orbital | Occupancy | Phosphate diester | Phosporothioate diester |
|---|---|---|---|
| $E_4$ |  | +1.1626 | +0.9812 |
| $E_3$ | ↑↓ | –0.8000 | –0.0061 |
| $E_2$ | ↑↓ | –1.0671 | –0.9563 |
| $E_1$ | ↑↓ | –1.6000 | –1.6000 |
| $E_0$ | ↑↓ | –2.2955 | –2.2187 |

The energies obtained for the π-electron orbitals of the internucleotide phosphorothioate diester and the internucleotide phosphate diester were similar for each level, except for $E_3$, the highest occupied molecular orbital (HOMO). The energy calculated for $E_3$ of the phosphorothioate diester was 0.0061β, compared to 0.8000β for $E_3$ of the phosphate diester.

Figure 4A:
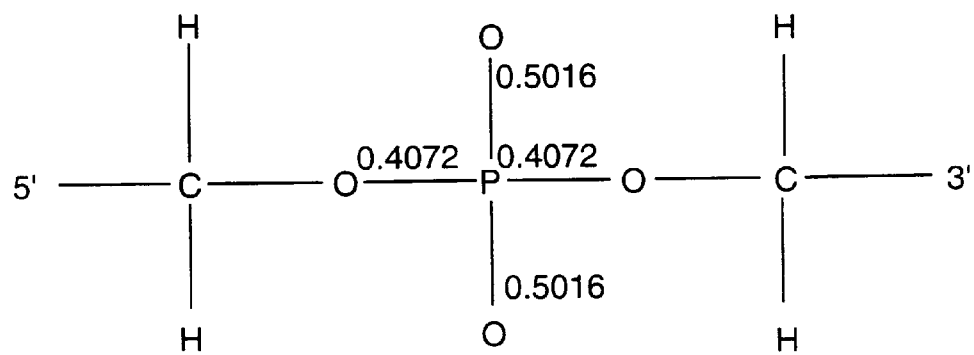
FIG. 4A is a diagram showing bond orders calculated for an internucleotide phosphate diester.
Figure 4B:
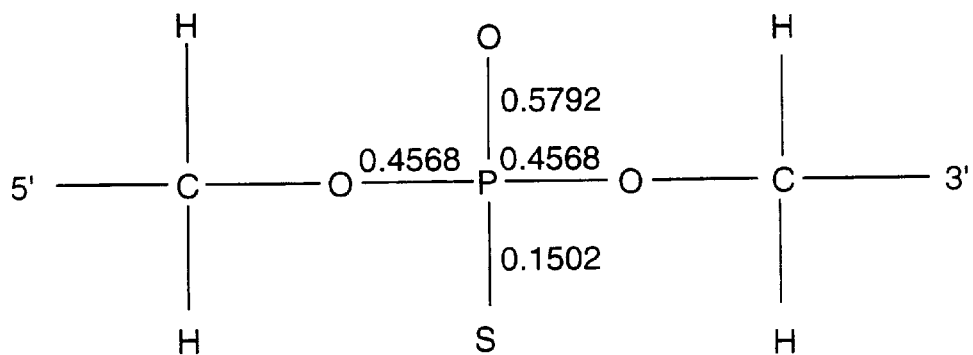
FIG. 4B is a diagram showing bond orders calculated for an internucleotide phosphorothioate diester.

The bond orders calculated for the internucleotide phosphate diester and the internucleotide phosphorothioate diester are shown in FIG. 4A and FIG. 4B, respectively. The phosphorothioate P-S bond integral (k5) was set to 0.1, yielding a P-S mobile bond order close to zero.

Figure 4C:
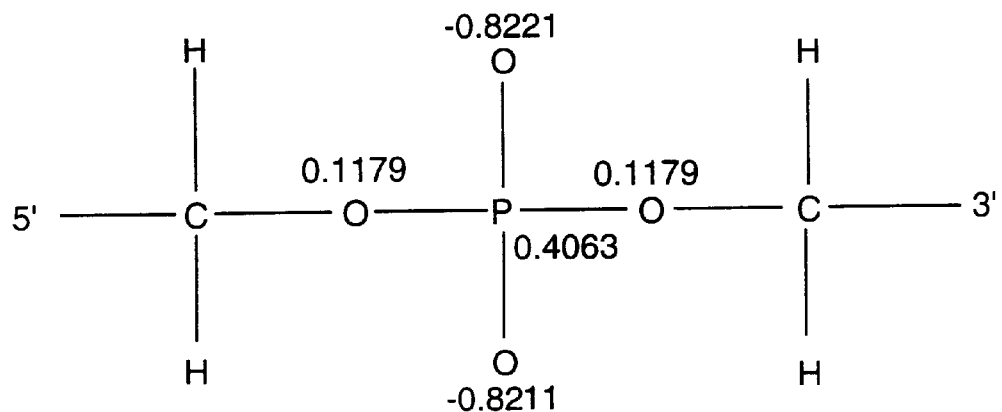
FIG. 4C is a diagram showing electronic charge distributions for an internucleotide phosphate diester.
Figure 4D:
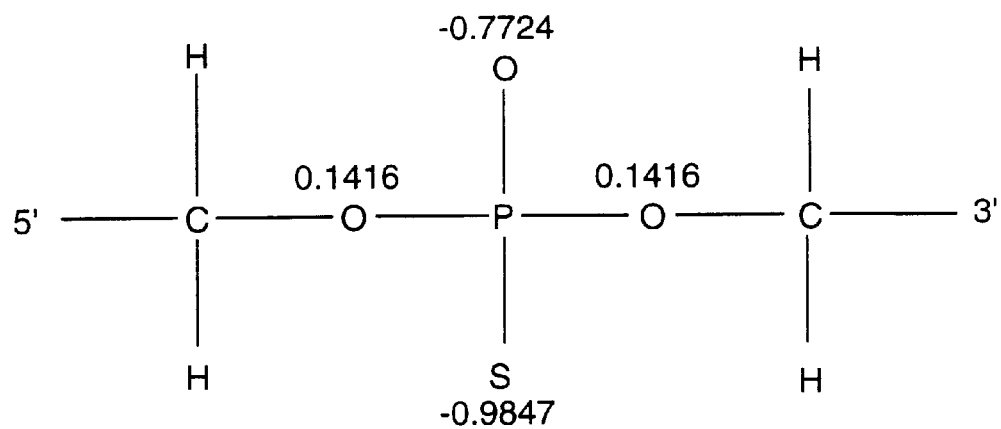
FIG. 4D is a diagram showing electronic charge distributions for an internucleotide phosphorothioate diester.

The electronic charge distributions for the internucleotide phosphate diester and the internucleotide phosphorothioate diester are shown in FIG. 4C and FIG. 4D, respectively. The coefficients of the π-electron orbitals of nucleotide diesters are shown in Tables IV and V. Numbers in parenthesis refer to the numbering scheme shown in FIG. 3.

TABLE IV

PHOSPHATE DIESTER

|  | P(1) | O(2) | O(3) | O(4) | O(5) |
|---|---|---|---|---|---|
| $E_4$ | –0.8386 | 0.2428 | 0.2991 | 0.2428 | 0.2991 |
| $E_3$ | 0.0000 | 0.0000 | 0.7071 | 0.0000 | –0.7071 |
| $E_2$ | –0.2280 | 0.3422 | –0.5974 | 0.3422 | –0.5974 |
| $E_1$ | 0.0000 | 0.7071 | 0.0000 | –0.7071 | 0.0000 |
| $E_0$ | –0.4948 | –0.5691 | –0.2316 | –0.5691 | –0.2316 |

TABLE V

PHOSPHOROTHIOATE DIESTER

|  | P(1) | O(2) | O(3) | O(4) | S(5) |
|---|---|---|---|---|---|
| $E_4$ | –0.8585 | 0.2661 | 0.3374 | 0.2661 | 0.0875 |
| $E_3$ | 0.0612 | –0.0307 | –0.0540 | –0.0307 | 0.9957 |
| $E_2$ | –0.2035 | 0.2529 | –0.9112 | 0.2529 | –0.0213 |
| $E_1$ | 0.0000 | 0.7071 | 0.0000 | –0.7071 | 0.0000 |
| $E_0$ | –0.4668 | –0.6036 | –0.2303 | –0.6036 | –0.0210 |

The $E_3$ molecular orbital was almost completely concentrated on the sulfur, with a coefficient for the sulfur atom equal to 0.9957.

The data described herein extends the semi-empirical Hückel molecular orbital analysis to phosphorothioate nucleotides. The orbital energies, bond orders, and electronic charge distributions shown above for the internucleotide phosphate diester agree very closely with standard determinations for phosphate anion and for nucleotide phosphate monoester. The energy of the highest occupied molecular orbital (HOMO) of the internucleotide phosphorothioate diester is 0.7939β (15.9 kcal/mole) higher than that of the corresponding orbital of the internucleotide phosphate diester (Table III). This relationship between the HOMOs of potential nucleophiles is consistent with the soft-nucleophile model of the internucleotide phosphorothioate diester. Soft nucleophiles react with soft targets by initiation through a mechanism that has been characterized as orbital-controlled. In the orbital-control model, the probability of reaction depends upon the iso-energicity and overlap of the HOMO of the electron donor (soft nucleophile) with the lowest unoccupied molecular orbital (LUMO) of the electron acceptor.

Orbital-control of initiation of the reaction between the internucleotide phosphorothioate diester and electrophile is further supported by the atomic coefficients of the highest occupied molecular orbitals given in Tables IV and V. The square of the coefficient for sulfur, atom 5 in $E_3$, the HOMO of the internucleotide phosphorothioate diester, is 0.9914. This high orbital density on the sulfur atom in the HOMO is compatible with the internucleotide phosphorothioate sulfur as the soft nucleophile electron-donor to the site of the nucleophilic attack.

The data described herein represents the first report of a molecular orbital analysis of internucleotide phosphorothioate diesters. The results are consistent with experimental reactivity of internucleotide phosphorothioate diesters calculated using other conventional methods. The results obtained from Hückel molecular orbital theory, are useful for predicting and rationalizing the degree and probability of reactivity of phosphorothioates with electrophiles. Further modification of oligonucleotides, e.g., methyliodide, methylamine, ethylamine, or propylamine, yield oligonucleotides that are taken up by target cells with increased efficiency.

EXAMPLE 4
Reaction of Adenosine 5'-Thiomonophosphate (AMPS) with a Carbodiimide Oligonuceotides, e.g., an IL-5 antisense oligonucleotide, with at least one PS internucleotide linkage can be further derivitized with an electrophilic agent, e.g., carbodiimide or iodoacetamide, in the presence of an excess of a nucleophilic agent, e.g., methylamine, ethylamine, propylamine, to yield an oligonucleotide that has the advantage of greater efficiency of uptake by cells. The product of this reaction is an oligonucleotide containing a non-bridging phosphoroamidate (PN) linkage. Such an oligonucleotide is resistant to nuclease degradation and enters cells with greater efficiency compared to an oligonucleotide with standard linkages. The presence of a PN linkage in an oligonucleotide also reduces chirality of the oligonucleotide. Moreover, the PN linkage is hydrolyzed under mildly acidic conditions such as those encountered intracellularly to yield an oligonucleotide with a standard phosphodiester (PO) linkage which binds to mRNA transcripts and inhibits protein expression. Alternatively, the nucleophilic agent is methyl iodide.

AMPS was reacted with carbodiimide and the products analyzed. $5.7 \times 10^{-3}$ M of AMPS (purchased from Sigma) was reacted with of 1.0 M of 1-ethyl-3-(3-dimethylaminopropyl) carbodiimide (EDC, purchased from Sigma) in $1 \times 10^{-1}$ M morpholino-ethanesulfonic acid buffer (MES, purchased from Sigma) at pH 6.1. A control AMPS solution lacking EDC was prepared in parallel. After 5 days at room temperature, the reaction and control solutions (in 10% deuterated water) were analyzed by $^{31}$P NMR using 85% phosphoric acid as an external reference.

As is discussed above, a parametricized semi-empirical Hückel molecular orbital analysis suggests that the phosphorothioate sulfur is a soft nucleophile. Carbodiimides are reagents that have been used to form reactive intermediates with nucleophiles such as carboxylate and phosphate anions. However, the reaction of carbodiimides with phosphorothioates has not previously been reported.

$^{31}$P NMR spectral analysis of the reaction of AMPS with EDC indicated that the singlet peak of AMPS had a chemical shift of 45.5 ppm with respect to phosphoric acid. The reaction of AMPS with EDC led to the disappearance of the 45.5 ppm peak and to the appearance of a new singlet peak with a chemical shift of 4.1 ppm. These data indicate that the reaction of the 5'-thiomonophosphate with carbodiimide leads to the desulfurization of the nucleoside thiomonophosphate with the production of the corresponding nucleoside monophosphate, e.g., as a result of the cleavage of the PS bond. Since the AMPS/EDC reaction was carried out under conditions in which the excess nucleophilic agent was $H_2O$ (rather than a reagent containing an amine group), a PO rather than a PN bond was generated.

Oligonucleotides modified to contain at least one PS or PN linkage are particularly well suited for clinical use because of their resistance to nuclease degradation and increased efficiency with which they enter cells.

The efficiency of cell uptake of post-synthesis modified antisense oligonucleotides is measured by contacting cells with various amounts of modified oligonucleotide (i.e., as described above for the dose-response assay) and measuring the level of expression of the target gene. A lower level of expression in the presence of a modified oligonucleotide compared to the same concentration of the corresponding unmodified oligonucleotide indicates that the modified oligonucleotide is more efficiently taken up by target cells.

Other embodiments are within the following claims.

We claim:

1. An oligonucleotide comprising at least one non-bridging phosphoroamidate internucleotide linkage, wherein said oligonucleotide inhibits IL-5 expression and wherein the sequence of said oligonucleotide is 5' ACTCAAATG-CAGAAGC 3' (SEQ ID NO:1).

2. An oligonucleotide comprising SEQ ID NO:1, said oligonucleotide comprising at least one non-natural internucleoside linkage, wherein said oligonucleotide inhibits expression of IL-5.

3. The oligonucleotide of claim 2, wherein said non-natural internucleotide linkage is a phosphorothioate linkage or a phosphoroamidate linkage.

4. The oligonucleotide of claim 2, wherein said non-natural internucleotide linkage is a phosphorothioate linkage.

5. The oligonucleotide of claim 2, wherein said oligonucleotide comprises a phosphorothioate linkage 3' to position 3 of SEQ ID NO:1 and a phosphorothioate linkage 3' to position 8 of SEQ ID NO:1.

6. A method of inhibiting IL-5 expression in vitro comprising contacting a cell with an antisense nucleic acid, wherein the nucleotide sequence of said antisense nucleic acid is complementary to a portion of the coding sequence of an IL-5 nucleic acid, wherein said antisense nucleic acid inhibits IL-5 expression in said cell.

7. The method of claim 6, wherein said antisense nucleic acid comprises at least one non-natural internucleotide linkage.

8. The method of claim 7, wherein said non-natural internucleotide linkage is a phosphorothioate linkage or a phosphoroamidate linkage.

9. The method of claim 7, wherein said non-natural internucleotide linkage is a phosphorothioate linkage.

10. The method of claim 9, wherein said antisense nucleic acid comprises a phosphorothioate linkage 3' to position 3 of SEQ ID NO:1 and a phosphorothioate linkage 3' to position 8 of SEQ ID NO:1.

11. An oligonucleotide consisting of the nucleotide sequence of SEQ ID NO:1.

* * * * *